(12) United States Patent
Ng et al.

(10) Patent No.: US 8,070,836 B2
(45) Date of Patent: Dec. 6, 2011

(54) COMBINED HOMOGENEOUS AND HETEROGENEOUS CATALYTIC TRANSESTERIFICATION PROCESS FOR BIODIESEL PRODUCTION

(75) Inventors: K. Y. Simon Ng, West Bloomfield, MI (US); Manhoe Kim, Troy, MI (US); Steven O. Salley, Grosse Pointe Park, MI (US)

(73) Assignee: Wayne State University, Detroit, MI (US)

( * ) Notice: Subject to any disclaimer, the term of this patent is extended or adjusted under 35 U.S.C. 154(b) by 471 days.

(21) Appl. No.: 12/252,875

(22) Filed: Oct. 16, 2008

(65) Prior Publication Data

US 2009/0145022 A1    Jun. 11, 2009

Related U.S. Application Data

(60) Provisional application No. 60/980,281, filed on Oct. 16, 2007.

(51) Int. Cl.
*C10L 1/18* (2006.01)
*C07C 51/00* (2006.01)
(52) U.S. Cl. ............ 44/308; 554/170; 554/169
(58) Field of Classification Search ........ 44/308
See application file for complete search history.

(56) References Cited

U.S. PATENT DOCUMENTS

| | | | |
|---|---|---|---|
| 4,161,463 A | 7/1979 | Myers et al. | |
| 5,354,878 A | 10/1994 | Connemann et al. | |
| 5,525,126 A * | 6/1996 | Basu et al. | 44/308 |
| 5,908,946 A | 6/1999 | Stern et al. | |
| 6,147,196 A * | 11/2000 | Stern et al. | 554/170 |
| 6,211,390 B1 * | 4/2001 | Peter et al. | 554/170 |
| 6,359,157 B2 | 3/2002 | Peter et al. | |
| 7,396,962 B1 | 7/2008 | Dubois et al. | |
| 7,655,818 B2 | 2/2010 | Dubois et al. | |
| 2003/0195367 A1 | 10/2003 | Barrault et al. | |
| 2007/0161828 A1 | 7/2007 | Kibino et al. | |
| 2010/0298586 A1 | 11/2010 | Dietrich et al. | |

FOREIGN PATENT DOCUMENTS

| | | |
|---|---|---|
| CN | 1836772 A | 3/2005 |
| DE | 3932514 A1 | 4/1991 |
| DE | 4123928 A1 | 1/1993 |
| DE | 4209779 C1 | 7/1993 |
| FR | 2882052 A1 | 8/2006 |

(Continued)

OTHER PUBLICATIONS

Babu, N. Seshu et al., "Room-Temperature Transesterification of Edible and Nonedible Oils Using a Heterogeneous Strong Basic Mg/La Catalyst," Energy & Fuels, 2008, vol. 22, pp. 1965-1971.

(Continued)

*Primary Examiner* — Cephia D Toomer
(74) *Attorney, Agent, or Firm* — Brinks Hofer Gilson & Lione

(57) ABSTRACT

In one aspect, a process for producing a biofuel comprises reacting a feed material that comprises a glyceride with an alcohol in the presence of a catalytic composition such that at least some of the glyceride in the feed material is converted into a biofuel mixture that comprises glycerol and the corresponding alcoholic ester of the glyceride. The catalytic composition comprises a heterogeneous catalyst and a homogeneous catalyst. The heterogeneous catalyst and the homogeneous catalyst have a synergistic effect in catalyzing the reaction of the glyceride in the feed material with the alcohol.

20 Claims, 9 Drawing Sheets

FOREIGN PATENT DOCUMENTS

| | | |
|---|---|---|
| FR | 2882053 A1 | 8/2006 |
| JP | 2006-104316 A | 6/2006 |
| JP | 2008-274030 A | 11/2008 |
| WO | WO 2008/012275 A1 | 1/2008 |
| WO | WO 2009/077161 A2 | 6/2009 |
| WO | WO 2010/085947 A1 | 8/2010 |

OTHER PUBLICATIONS

Kawashima, Ayato et al., "Development of heterogeneous base catalysts for biodiesel production," Bioresource Technology, vol. 99, 2008, pp. 3439-3443.

Li, Xu et al., "A novel solid superbase of $Eu_2O_3Al_2O_3$ and its catalytic performance for the transesterification of soybean oil to biodiesel," Catalysis Communications, 8, 2007, pp. 1969-1972.

Yan, Shuli et al., "Simultaneous transesterification and esterification of unrefined or waste oils over $ZnO-La_2O_3$ catalysts," Applied Catalysis A: General, vol. 353, 2009, pp. 203-212.

International Search Report for International Application No. PCT/DE2010/000109, dated Jul. 15, 2010, 4 pages.

D. E. Lopez, J. G. Goodwin Jr., D. A. Bruce, E. Lotero, Appl. Catal. A: Gen. 295(2005) 97.

A. C. Pinto, L. L. N. Guarieiro, M. J. C. Rezende, N. M. Ribeiro, E. A. Torres, W. A. Lopes, P. A. de P. Pereira, J. B. Andrade, J. Braz. Chem. Soc. 16(6B)(2005) 1313.

M. D. Serio, M. Ledda, M. Cozzolino, G. Minutillo, R. Tesser, E. Santacesaria, Ind. Eng. Chem. Res. 45(2006) 3009.

W. Xie, H. Peng, L. Chen, J. Mol.Catal. A: Chem. 246(2006) 24.

G. J. Suppes, M. A. Dasari, E. J. Doskoscil, P. J. Mankidy, M. J. Goff, Appl. Catal. A: Gen. 257(2004) 213.

K.-J. Kim, B.-S. Kang, M.-J. Kim, Y. M., Park, D.-K. Kim, D.-K. Kim, J.-S. Lee, K.-Y. Lee, Catal. Today 93-95(2004) 315.

R. S. Watkins, A. F. Lee, K. Wilson, Green Chem. 6(2004) 335.

C. C. S. Macedo, F. R. Abreu, A. P. Tavares, M. B. Alves, L. F. Zara, J. C. Rubim, P. A. Z. Suarez, J. Braz. Chem. Soc. 17(7)(2005) 1291.

H. Li, W. Xie, Catal. Lett. 107(1-2)(2006) 25.

L. Bournay, D. Casanave, B. Delfort, G. Hillion, J. A. Chodorge, Catal. Today 106(2005) 190.

W. Xie, H. Peng, L. Chen, Appl. Catal. A: Gen. 300(2006) 67.

S. Gryglewicz, Bioresour. Technol. 70(1999) 249.

M. L. Granados, M. D. Z. Poves, D. M. Alonso, R. Mariscal, F. C. Galisteo, R. Moreno-Tost, J. Santamaria, J.L.G. Fierro, Appl. Catal. B: Environmental 73(2007) 317-326.

H. Hattori, J. Japan Petrol. Inst. 47(2)(2004) 67.

N. Shibasaki-Kitakawa, H. Honda, H. Kuribayashi, T. Toda, T. Fukumura, T. Yonemoto, Bioresour. Technol. 98(2007) 416.

G. Vicente, A. Coteron, M. Martinez, J. Aracil, Ind. Corps Prod. 8(1998) 29.

AG1, AG MP-1 and AG2 Strong Anion Exchange Resin Instruction Manual (Lit 212 Rev C), Bio-Rad (Hercules, CA 84547).

J. V. Gerpen, B. Shanks, R. Pruszko, D. Clements, G. Knothe, National Renewable Energy Laboratory Report NREL/SR-510-36244 (2004).

F. X. McGarvey, E. W. Hauser, B. Bachs, J Stellitano, Proc. Int. Water Conference, IWC-879(1987) 93.

Dowex Ion Exchange Resins (Form No. 177-01751-602XQRP) Dow Chemical USA, Jun. 2002, 2 pg.

\* cited by examiner

COMBINED HOMOGENEOUS AND HETEROGENEOUS CATALYTIC TRANSESTERIFICATION PROCESS FOR BIODIESEL PRODUCTION

The present application claims priority to U.S. Provisional Patent Application No. 60/980,281, filed Oct. 16, 2007, the entirety of which is hereby incorporated by reference.

FIELD OF THE INVENTION

The present invention relates to a method for the production of biodiesel through transesterification of raw materials, such as vegetable oils and animal fats, with alcohol. More specifically, the present invention relates to a combined homogeneous and heterogeneous catalytic transesterification process for biodiesel production.

BACKGROUND OF THE INVENTION

Since traditional fossil energy resources are limited, research is being directed towards the use of alternative renewable fuels. One of the approaches is the conversion of vegetable oils and animal fats into biodiesel. Vegetable oils and animal fats are comprised of complex mixtures of triglycerides (TGs) and other relatively minor components, such as free fatty acids (FFAs), gums, waxes, etc. Biodiesel is usually made through a chemical process called transesterification, whereby TGs react with methanol in the presence of a catalyst to produce a complex mixture of fatty acid alkyl esters (biodiesel) and glycerol.

Many of the commercial biodiesel that are currently produced in the U.S. come from the transesterification of soybean oil using homogeneous base (such as NaOH or KOH) catalyzed processes. Alkali cations are removed after the transesterification reaction as alkali soaps in glycerol phase. An acidic neutralization step with aqueous acid is required to neutralize these salts. Even though homogeneous catalyzed biodiesel production processes are relatively fast and show high conversions, usage of homogeneous base catalyst suffers from the formation of undesirable side reaction such as saponification which creates problems in product separation and ultimately lowers the ester (biodiesel) yield.

In order to minimize problems associated with the homogeneous catalytic processes, attempts have been made to develop heterogeneous catalyst systems in transesterification of triglycerides. Solid base catalysts are used to replace alkaline homogeneous catalysts, to minimize soap formation, separation, corrosion and environmental problems. At the laboratory scale, many different heterogeneous catalysts have been reported, including MgO, hydrotalcites, zeolites loaded with sodium oxide, Li/CaO, KF/ZnO, mixed metal oxides ($Al_2O_3$—SnO, $Al_2O_3$—ZnO), $Zn/I_2$, mixed oxide of zinc and aluminum, and potassium loaded alumina. Catalytic activities of the heterogeneous base catalysts in the transesterification of soybean oil show a correlation with their corresponding basic strengths. Although alkali metal-containing catalysts show strong basicities, alkali metal ions are easily dissolved in the reaction media. Thus, reaction proceeds according to homogeneous mechanism. Other solid metal oxides such as those of tin, magnesium, and zinc are known heterogeneous catalysts but again function according to a homogeneous mechanism leading to metal soaps or metal glycerates.

Much work has focused on the preparation of solid catalysts possessing strong basic sites. Strong basic sites are generated by removal of water or acidic gas molecules by pretreatment at high temperatures. These basic sites are fragile and can be easily contaminated by moisture, oxygen, carbon dioxide, and other gaseous substances when exposed to air. As a result, the exposed surface does not exhibit their intrinsic catalytic activities. Up to now, conversions of most heterogeneous catalysts are not high enough to be used for the industrial scale biodiesel production. In comparison with homogeneous catalysts, relatively prolonged reaction periods are required in heterogeneous catalytic process. The Esterfif-H process is one of the few known processes which claims to have comparable performance as the homogeneous catalytic process.

BRIEF SUMMARY OF THE INVENTION

In one aspect, a process for producing a biofuel comprises reacting a feed material that comprises a glyceride with an alcohol in the presence of a catalytic composition such that at least some of the glyceride in the feed material is converted into a biofuel mixture that comprises glycerol and the corresponding alcoholic ester of the glyceride. The catalytic composition comprises a heterogeneous catalyst and a homogeneous catalyst. The heterogeneous catalyst and the homogeneous catalyst have a synergistic effect in catalyzing the reaction of the glyceride in the feed material with the alcohol.

In another aspect, a process for producing a biofuel comprises contacting a feed material that comprises a glyceride with a heterogeneous catalyst, heating the feed material and the heterogeneous catalyst, adding an alcohol and a homogeneous catalyst to the feed material and the heterogeneous catalyst, and allowing the glyceride in the feed material and the alcohol to react to produce the corresponding alcoholic ester of the glyceride.

In yet another aspect, a process for producing a biofuel comprises converting a feed material that comprises a glyceride, in the presence of an alcohol, into glycerol and the corresponding ester of the glyceride using a heterogeneous resin catalyst combined with a homogeneous catalyst.

DETAILED DESCRIPTION OF THE PREFERRED EMBODIMENTS

Figure 1:
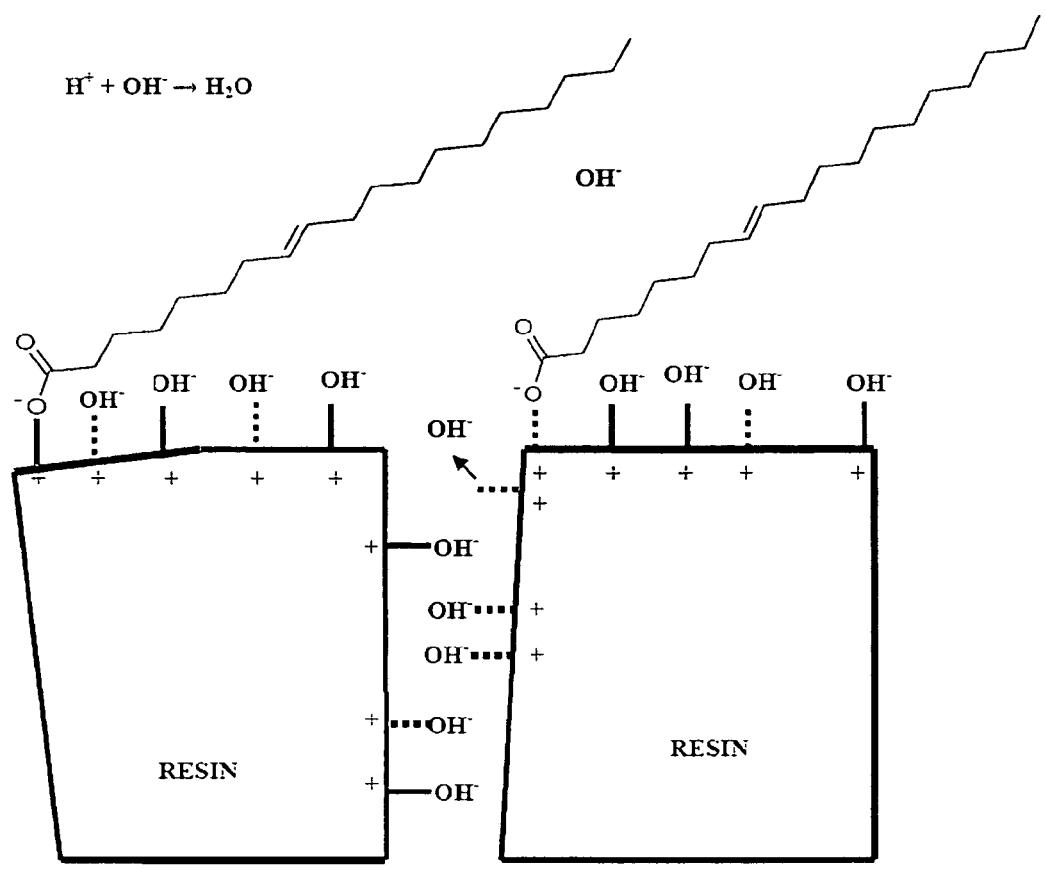
FIG. 1 is a schematic diagram illustrating the active sites of the resin catalyst in acidic or neutral medium.

Strong anion exchange resins can be used as basic catalysts for biodiesel synthesis. For example, anion- and cation-exchange resins were utilized in the transesterification reaction of sun flower oil to biodiesel, but the conversion was less than about 1% after about 8 hours reaction at about 333 K. For example, a batch transesterification reaction of triolein with ethanol was conducted using various ion exchange resins produced by Mitsubishi Chemical Company. The best catalytic performance was obtained from the resin having a porous structure, the lowest cross-linking density, and the smallest particle size. Over about 80% conversion to ethyloleate was obtained after about 10 hours reaction at about 323 K. A cation ion exchange resin, Amberlyst-15, was also tested as an acid catalyst for transesterification of triacetin with methanol. A conversion of about 50% of triacetin was resulted after about 150 minutes at about 333 K.

One of the issues during biodiesel production is the completeness of the transesterification reaction. The ASTM D 6584 specification of the final biodiesel product requires that the total glycerol be less than about 0.24%. If the reaction is incomplete, then there will be triglycerides, diglycerides, and monoglycerides left in the reaction mixture. Each of these compounds still contains a glycerol molecule that has not been released. Un-reacted glycerides contained in biodiesel may cause problems during storage or in the fuel system. A high total glycerin content can lead to injector fouling and may also contribute to the formation of deposits on injection nozzles, pistons, and valves. Thus, catalytic processes leading to near complete transesterification reactions are required in order to be used in commercial biodiesel production. The ASTM specification can be fulfilled by using homogeneous catalyst such as NaOH. The ASTM specification on the resulting biodiesel cannot be fulfilled by using most, if not all, conventional heterogeneous catalysts. The Esterfif-H process is one of the few known processes which claims to replace homogeneous catalytic processes successfully.

However, in some, if not all, of the conventional methods, about 1% sodium hydroxide of soybean oil weight is used when the free fatty acids level is less than about 1%. When free fatty acids level is above about 1%, higher weight percent of alkali catalyst is needed to neutralize the free fatty acids. However, a large amount of waste water is produced in order to separate and clean the catalyst and product. Moreover, the amount of soap formed increased with increasing alkali catalyst used. Also, the soaps formed in the process may allow emulsification that causes phase separation of the glycerol and esters to be less sharp. Soap formation also produces water that hydrolyzes the triglycerides and contributes to the formation of more soap. Further, catalyst that has been converted to soap is no longer available to accelerate the reaction. Thus, it is desirable to minimize the amount of alkali catalyst used. On the other hand, the heterogeneous catalyst does not produce soap through free fatty acid neutralization or triglyceride saponification. However, the performance of heterogeneous catalyst is still unfavorable compared to that of the alkali homogeneous catalysts.

According to one embodiment of the present invention, it is provided a novel approach to combine the merits of homogenous and heterogeneous catalytic processes to improve the efficiency of the transesterification process, and the quality of biodiesel products. This approach minimizes the drawbacks of the conventional homogeneous process such as soap formation, which makes separation of methyl esters difficult. This approach will also minimize the waste water produced in order to separate catalyst dissolved and to wash the product. On the other hand, this approach overcomes low catalytic activity and long reaction times often observed for heterogeneous catalysts.

The novel method is based on the activation of heterogeneous catalysts in basic environment, by co-processing with a trace level of homogeneous catalysts. Theoretically, basic sites of heterogeneous catalysts are not insoluble and are easily quenched or become inactive in acidic environment. However, if the environment becomes basic with a trace level of homogeneous catalysts such as $CH_3ONa$, KOH, and NaOH, then the catalytic active sites of heterogeneous resin become active. The catalytically active hydroxide ion can be transferred from and to between reactants and catalyst surfaces.

Heterogeneous base catalysts are defined as insoluble solid catalysts with electron rich surface. Examples of heterogeneous basic catalysts include, but are not limited to, anion exchange resins, mixed metal oxides, mixed metal oxides loaded on supports such as alumina, silica-alumina, zeolites, carbon materials. Homogeneous catalysts are defined as soluble basic catalysts. Examples of homogeneous catalysts include, but are not limited to, alkali and alkali earth compounds such as NaOH, KOH, $Ca(OH)_2$, and alkali alkoxides.

Strong anion exchange resins can be classified as type 1 and type 2. Type 1 is quaternized amine products made by the reaction of trimethylamine with the copolymer of styrene and divinylbenzene. Type 1 functional group is one of the strongest basic functional group available. Type 2 functionality is obtained by the reaction of the styrene-divinylbenzene copolymer with dimethylethanolamine. Type 2 resin has lower basicity than Type 1, yet the efficiency of regeneration of the type 2 resin to the hydroxide form is higher than that of type 1 resin. Type 1 resins have better chemical stability than Type 2, and are being favored for relatively high temperature application. The type 1 resins can be classified as gel type (such as Marathon A, Monosphere 550A, and DOWEX) and macroporous type (such as Marathon MSA and Amberite 900) according to their structure and porosity. Gel type structure exhibits microporosity with pore sizes typically up to about 10 or about 15 Å, and macroporous type has considerably larger pore diameters, up to several hundred Angstroms, and their surface area reaches about 500 $m^2/g$ or higher.

In one embodiment, a process for producing a biofuel comprises reacting a feed material that comprises a glyceride with an alcohol in the presence of a catalytic composition such that at least some of the glyceride in the feed material is converted into a biofuel mixture that comprises glycerol and the corresponding alcoholic ester of the glyceride. The catalytic composition comprises a heterogeneous catalyst and a homogeneous catalyst.

Preferably, the heterogeneous catalyst and the homogeneous catalyst have a synergistic effect in catalyzing the reaction of the glyceride in the feed material with the alcohol. Preferably, the homogeneous catalyst is a co-catalyst that maintains a basic local environment in which the heterogeneous catalyst is activated.

The feed material can be a fatty acid triglyceride. Preferably, the feed material is a vegetable oil, an animal fat, or combinations thereof. More preferably, the feed material is a soybean oil, a sun flower oil, a triolein, a triacetin, or combinations thereof.

Any suitable heterogeneous catalysts can be used. For example, the heterogeneous catalyst can be an exchange resin, a metal oxide, or combinations thereof. Preferably, the exchange resin is an anion exchange resin or a cation exchange resin. More preferably, the exchange resin is an anion exchange resin. Even more preferably, the anion exchange resin is a basic anion exchange resin.

The anion exchange resin can be a quaternized amine. Preferably, the quaternized amine is a trimethylamine quaternized with a styrene-divinylbenzene copolymer, a dimethylethanolamine quaternized with a styrene-divinylbenzene copolymer, or combinations thereof. The anion exchange resin can be a gel type anion exchange resin, a macroporous type anion exchange resin, or combinations thereof.

Preferably, the gel type anion exchange resin has an average pore size of up to about 10 or about 15 Å. Preferably, the macroporous type anion exchange resin has an average pore size of up to about 1,000 Å. Preferably, the macroporous type anion exchange resin has an average surface area of at least about 500 $m^2/g$. Preferably, less than about 4% of the exchange resin is cross-linked. More preferably, less than about 2% of the exchange resin is cross-linked. Even more preferably, substantially no exchange resin is cross-linked. Preferably, the exchange resin has an average particle size of from about 650 μm to about 75 μm.

The metal oxides can be loaded on a support. The support can be alumina, silica-alumina, zeolite, carbon material, or combinations thereof. Preferably, the heterogeneous catalyst is tin oxide, magnesium oxide, zinc oxide, hydrotalcite, zeolite loaded with sodium oxide, Li/CaO, KF/ZnO, $Zn/I_2$, potassium loaded alumina, mixed metal oxides, or combinations thereof. Preferably, the mixed metal oxides are $Al_2O_3$—SnO, $Al_2O_3$—ZnO, zinc oxide and aluminum oxide, or combinations thereof.

Any suitable homogeneous catalysts can be used. For example, the homogeneous catalyst can be an alkali compound, an alkali earth compound, or combinations thereof. Preferably, the alkali compound is an alkali hydroxide, an alkali alkoxide, or combinations thereof. More preferably, the alkali hydroxide is NaOH, KOH, $Ca(OH)_2$, or combinations thereof. Preferably, the alkali alkoxide is $CH_3ONa$. Preferably, the alkali alkoxide can be an about 0.020 M $CH_3ONa$ solution in methanol.

Preferably, the homogeneous catalyst is no more than about 1% of the feed material weight. More preferably, the homogeneous catalyst is no more than about 0.02% of the feed material weight. Preferably, the mass ratio of the catalyst composition to the feed material is about 1:3. Preferably, the molar ratio of the alcohol to the feed material is from about 1:1 to about 20:1. More preferably, the molar ratio of the alcohol to the feed material is about 7:1.

In one embodiment, the feed material is converted to a biofuel by contacting the feed material with the heterogeneous catalyst, heating the feed material and the heterogeneous catalyst, adding the alcohol and the homogeneous catalyst to the feed material and the heterogeneous catalyst to obtain a reaction mixture, and allowing the reaction mixture to react.

Preferably, the reaction mixture is incubated for a period of time such that a substantial portion of the glyceride in the feed material is converted into the corresponding alcoholic ester of the glyceride before a saponification side reaction is substantially started. Preferably, the feed material is heated to about 328 K.

The process for producing a biofuel can further comprise removing some or substantially all of the glycerol from the biofuel mixture to provide a raw biofuel. The process can also comprise rinsing the raw biofuel with water to provide the biofuel.

Preferably, no less than about 60% of the feed material is converted to the biofuel. More preferably, no less than about 80% of the feed material is converted to the biofuel. Even more preferably, no less than about 90% of the feed material is converted to the biofuel.

In another embodiment, a process for producing a biofuel comprises contacting a feed material that comprises a glyceride, and converting the glyceride in the feed material to glycerol and a raw biofuel. The conversion comprises contacting the feed material with a heterogeneous catalyst, heating the feed material and the heterogeneous catalyst, adding an alcohol and a homogeneous catalyst to the feed material and the heterogeneous catalyst, and allowing the glyceride in the feed material and the alcohol to react to produce the corresponding alcoholic ester of the glyceride. The process for producing a biofuel can further comprise separating the glycerol from the raw biofuel, and cleaning the raw biofuel to provide the biofuel.

Preferably, the heterogeneous catalyst is an ion-exchange resin, the homogeneous catalyst is a soluble base, and the alcohol is a low alkyl alcohol. Low alkyl alcohol can be any alcohol that contains 1-20 carbon atoms. The carbon atoms can be joined together in straight or branched chains or in rings, either saturated or unsaturated.

In a further embodiment, a process for activating an ion-exchange resin catalyst comprises ion-exchanging the ion-exchange resin catalyst in an alkali hydroxide solution, leaching the ion-exchange resin catalyst in an alcohol after ion-exchanging, removing physically absorbed alkali hydroxide from the ion-exchange resin, and washing the ion-exchange resin with the alcohol.

Preferably, the alkali hydroxide solution is an alcoholic solution. More preferably, the alkali hydroxide solution is a methanolic solution. Preferably, the leaching is carried out in substantially pure methanol.

In yet another embodiment, a process for regenerating a used ion-exchange resin catalyst comprises ion-exchanging the used ion-exchange resin catalyst in an alkali hydroxide solution, leaching the ion exchanged ion-exchange resin catalyst in an alcohol, removing physically absorbed alkali hydroxide from the leached ion-exchange resin, and washing the leached ion-exchange resin with the alcohol.

In further another embodiment, a process for producing a biofuel comprises converting a feed material that comprises a fatty-acid glycerides, in the presence of an alcohol, into glycerol and fatty acid ester of the alcohol using a heterogeneous resin catalyst combined with a homogeneous catalyst. The process for producing a biofuel can further comprise separating the glycerol from the fatty acid ester of the alcohol, and cleaning the fatty acid ester to provide the biofuel.

Strongly basic anion exchange resins can be used as heterogeneous catalyst for transesterification reaction of soybean oil with methanol. Gel types of resins usually have higher basic site densities than macroporous resins. However, high catalytic activities were observed in the macroporous resins possibly due to those macroporous structures. The basic site catalytic activities of the anion exchanged resins also depended on the pH value of the reaction medium. The catalytic activities of the resins were highly restricted or deactivated in an acidic or neutral medium due to neutralization of the basic sites and adsorbed organic anions on the surface of the catalyst. The catalytic activities were increased in basic environment because the deactivated sites in an acidic or neutral solution became activated by a trace amount of homogeneous base. This approach can not only minimize soap formation by using heterogeneous catalyst but also overcome the limitations of heterogeneous catalyst.

Catalytic activity of the resin was shown to be related with the degree of cross-linking or particle size of the resin. Lower cross-linking degree tends to give larger pore aperture and larger number of active sites. Smaller particle size tend to give a larger catalytic surface area. The resin which has lower degree of cross-linking and smaller particle size tends to give better activity. The preferred methanol to oil ratio for the completion of reaction was about 7:1 according to embodiments of the invention. The used resin catalyst can be recycled through a regeneration process. The regeneration efficiency of the gel type resin was typically higher than that of the macroporous resin.

EXAMPLES

Reagents

Anhydrous methyl alcohol (about 99.8%) and sodium hydroxide (about 99%) were obtained from Mallinckrodt Chemicals (Phillipsburg, N.J.). Commercial, edible grade soybean oil (total acid number was about 0.046 mg KOH/g) was obtained from a grocery store (COSTCO) and evacuated in a vacuum to remove water and gases dissolved in the oil phase. Strong basic anion exchange resins were purchased from Sigma-Aldrich (St. Louis, Mo.). Marathon A and Monosphere 550A were purchased in hydroxide form, and the other resins were in chloride form. Table 1 summarizes the physical properties and the exchange capacity of the resins studied. The gel type resins (DOWEX 1×2, 1×4) having different cross-linking degree and different particle size were also purchased from Sigma-Aldrich.

TABLE 1

Properties of Resins.

| Resins | Matrix | Particle size | Cross-linking (%) | Exchange Capacity (meq/ml) |
|---|---|---|---|---|
| Marathon A | Gel | 610 ± 50 µm | — | 1.2 |
| Monosphere 550 A | Gel | 590 ± 50 µm | — | 1.1 |
| Marathon MSA | Macroporous | 640 ± 50 µm | — | 1.0 |
| Amberite 900 | Macroporous | 300-1200 µm | — | 1.0 |
| DOWEX 1x4 | Gel | 75-150 µm | 4 | 1.0 |
| DOWEX 1x2 | Gel | 150-300 µm | 2 | 0.7 |
| DOWEX 1x2 | Gel | 75-150 µm | 2 | 0.6 |

Resin Catalyst Preparation

About 100 g of Marathon MSA, Amberite 900, Dowex 1×2, and Dowex 1×4 (received as chloride form) resins were ion-exchanged in about 1.0 M NaOH solution (about 250 mL) in methanol for about 12 hours. This ion exchange process was repeated four times because the chloride ion had a higher selectivity (about 22 times) to the resin than hydroxide ion. Marathon A and Marathon MSA resins (received as hydroxide form) were activated in about 1.0 M NaOH solution in methanol for about 12 hours. The same activation process was used to regenerate the basic sites of the used catalysts. All the ion-exchanged, activated, and regenerated resins (about 10 g) were then leached in pure methanol for about 12 hours and then filtered in order to remove physically absorbed NaOH. Finally, all the resins were washed with methanol in a filtering trap before used as catalysts.

The density of the basic sites of the resin was determined by the following titration method. About 5.0 g of resin (swelled and wetted with methanol) was added into a flask containing about 40 mL of de-ionized water. About 1.000 mL of hydrochloric acid (about 12.1 N) was added to the flask. The flask was put aside for about 12 hours at room temperature in order to neutralize the hydroxide form of resin. After neutralization the resin was filtered out from the solution, the hydrochloric acid remaining in the solution was titrated with about 1.0 M NaOH solution.

Transesterification Procedure and Analysis Methods

Erlenmeyer flasks (about 125 mL) containing soybean oil, methanol, resin catalysts were used as batch reactors. In most studies, a molar ratio of about 10 methanol/soybean oil, and a mass ratio of about 1:3 in catalyst/soybean oil were used. Moreover, about 5.1 mL of about 0.02 M $CH_3ONa$ solution in methanol as a homogeneous catalyst was added to about 30.0 g of soybean oil. Flasks containing soybean oil and resin catalyst were heated in a shaking bath maintained at about 328 K. Methanol and sodium methoxide solution were added to the flasks. The flasks containing reaction mixtures were capped with glass stoppers and sealed with vacuum grease. The flasks were kept in the incubator (Series 25 incubator, New Brunswick Scientific CO.) with a shaking speed of about 350 rpm. At fixed time intervals, about 1.0 mL of the sample was withdrawn from the mixtures by using syringes equipped with filter (with a pore size of about 0.45 µm). The sample solutions collected in small vials were first dried in a hood to remove dissolved methanol. The upper portion of the sample (methyl ester phase) was taken for GC analysis. Since triglyceride saponification can be slight when sodium methoxide and heterogeneous catalysts are used as catalysts, the biodiesel yield (%) can be defined as total weight percent of fatty acid methyl esters from the weight of product after removing methanol and free glycerol. Fatty acid methyl esters in the samples were quantified by using a GC-MS (Clarus 500 GC-MS, Perkin-Erlmer) with a capillary column (Rtx-WAX Cat. No. 12426). Ethyl arachiate (Nu-Chek Prep Inc, Elysian, Minn.) was used as an internal standard.

Density of the Basic Sites of the Resins

Resin ion exchange is usually carried out in aqueous solution because resins are ionic compounds. However, resin can absorb water molecules which interfere with the transesterification reaction and thus result in poor yields and high level of soap, free fatty acids, and triglycerides in the final product. In order to minimize negative effects of water, about 1.0 M NaOH solution in methanol instead of about 1.0 M NaOH aqueous solution was used in the ion-exchange process.

TABLE 2

Densities of the basic site of the resins ion exchanged in 1.0 M NaOH in methanol

| Resin catalysts | Before reaction (mmol/g) | After reaction (mmol/g) |
|---|---|---|
| Marathon A | 1.70 | 1.57 |
| Monosphere 550A | 1.47 | 1.40 |
| Marathon MSA | 0.50 | 0.43 |
| Amberite 900 | 0.54 | 0.43 |
| Dowex 1x4/75~150 µm | 0.60 | 0.53 |
| Dowex 1x2/150~300 µm | 0.62 | 0.57 |
| Dowex 1x2/75~150 µm | 0.66 | 0.58 |

Table 2 shows the densities of the basic site of the resins before and after reaction. The densities of the base sites of the Marathon A and Monosphere 550A were about three times higher than that of macroporous resins. Macroporous resins or cross-linked resins are known to have lower basic site densities. After a batch reaction, the densities of the basic sites were decreased by about 5% to about 20% of the initial values during a batch reaction. The percentage loss of basic sites in macroporous resins (about 14% for Marathon MSA and about 20% for Amberite 900) were larger than those in the gel phase resins (about 7% for Marathon A and about 5% Monosphere 550A). The higher loss of hydroxide on macroporous resin can be attributed to two possible causes: either thermal decomposition of the basic sites (ammonium functional groups) during catalytic reaction, or ion exchange with organic ions such as oleates, linoleates, and linolenates evolved during reaction.

The Synergy Effect of Heterogeneous Catalyst and Homogeneous Catalyst on the Transesterification of Soybean Oil with Methanol Two different batch experiments, with and without $CH_3ONa$, were investigated to study the synergic effect of homogeneous catalyst on the heterogeneous process. In one batch, about 5.1 mL of about 0.02 M $CH_3ONa$ solution in methanol was added to about 30.0 g of soybean oil (acid number: about 0.046 mg KOH/g). In the other batch, no $CH_3ONa$ solution was added for comparison purpose. The molar ratio of methanol to soybean oil was about 10:1. In the first batch, free fatty acid contained in soybean oil reacts with some of $CH_3ONa$, and converted to $CH_3OH$ and organic sodium salt (soap). Given the amount of $CH_3ONa$ added to the reaction mixture was about 0.018 wt %, only about 0.003 wt % may be consumed during neutralization. Thus, the amount of $CH_3ONa$ added corresponded to about 0.014 wt % NaOH. Compared to about 1.0 wt % sodium hydroxide used in the conventional homogeneous method, about 0.014% sodium hydroxide was much lower.

The active sites of heterogeneous catalyst are not insoluble. Although resin catalysts have a lot of basic sites, only a small portion of the sites can be used as catalytic sites because triglyceride molecules are too big to go into the micropores of the gel type resin. Some of the basic sites located on the outer surface of the resin is relatively stronger according to their favorable geometric and electrical environments. Strong basic sites are catalytically more effective. The strong basic sites can afford free hydroxide ion or take it back. Firstly, small amount of the strong basic sites can be neutralized by free fatty acids contained in the feed reactants. The organic anions resulted adhere to the resin surface by electrostatic forces and block the entrances to the micropores. The remained basic sites can be used as catalytic sites for transesterification.

Referring to FIG. 1, a certain part of the basic sites could be ion exchanged with organic anions generated during catalytic transesterification reaction. The organic anions bonded on the surface of the resin could be removed by the ion-exchange or activation in a NaOH (about 1 M) solution in methanol. Released organic anions could be actually observed at the regeneration process. Deactivation of resin catalyst was more profound in an acidic or neutral medium than in a basic medium. Thus, the catalytic activities of the resins were low in acidic or neutral medium. However, the reaction medium maintained in a basic environment, the bound organic anions can be reacted further to methyl esters. Thus, the catalytic active sites of heterogeneous resin can remain highly active. The catalytically active hydroxide ion can be transferred between reactants and catalyst surfaces.

Figure 2:
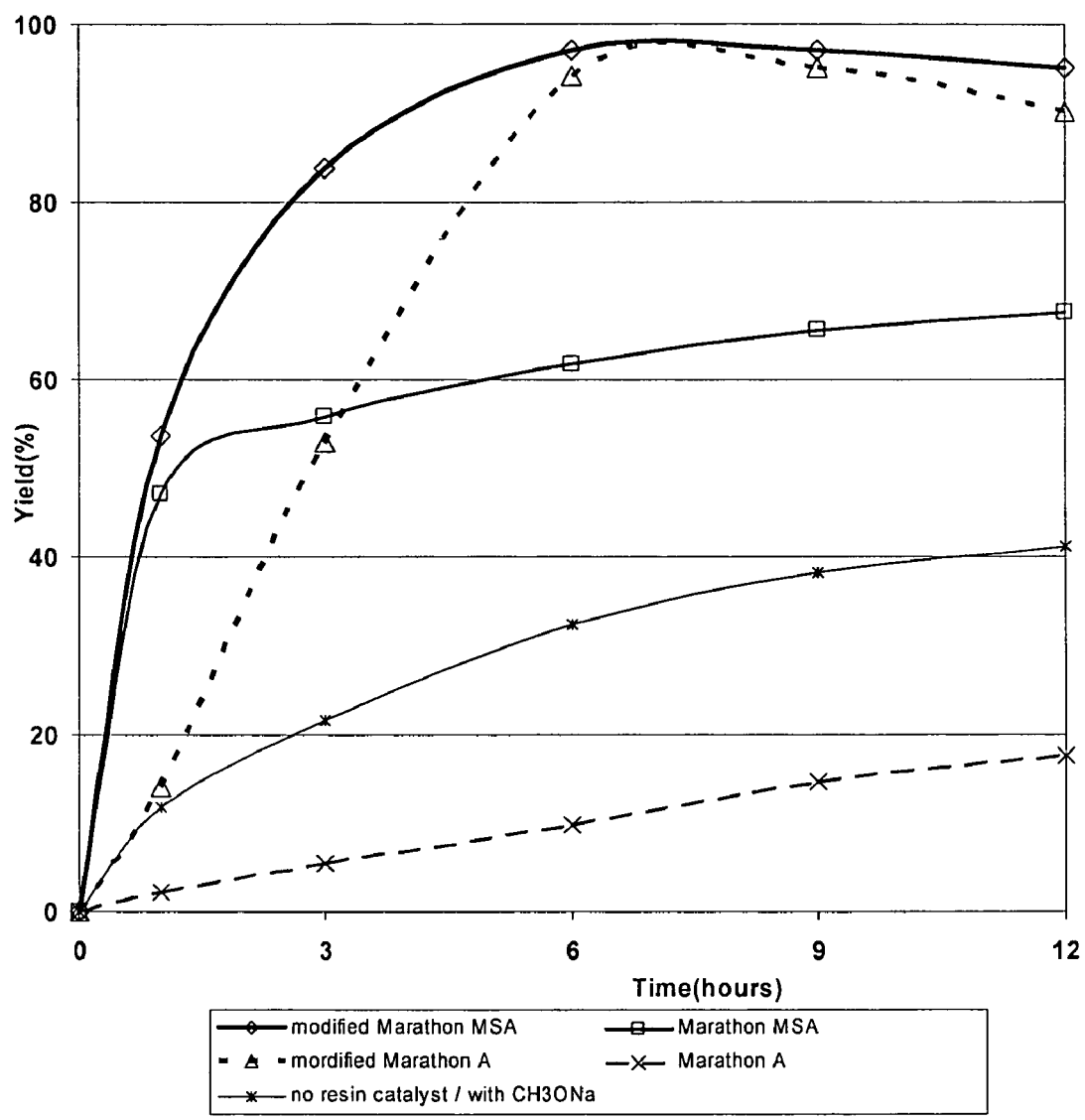
FIG. 2 is a diagram illustrating the synergy effect of heterogeneous catalyst and homogeneous catalyst on the transesterification of soybean oil with methanol.

Referring to FIG. 2, the yields approached to about 100% after about 6 hours at about 328 K with activated resin catalyst and $CH_3ONa$. The reaction was carried out with about 30 g of soybean oil (about 5.1 mL of about 0.020 M $CH_3ONa$ solution in methanol was added when $CH_3ONa$ was used), a methanol/oil molar ratio of about 10:1, at a reaction temperature of about 326 K, and a shaking speed of about 350 rpm. With about 0.018 wt % of homogeneous catalyst ($CH_3ONa$) only, the reaction could not go to completion. When both Marathon A (or Marathon MSA) and about 0.018 wt % $CH_3ONa$ were used together, reaction went to completion. The enhanced activity observed can not be attributed to a mere addition of the $CH_3ONa$ catalytic activity and the resin catalytic activity. It should be noted that $CH_3ONa$ was a co-catalyst maintaining the basic environment where the heterogeneous catalyst could be active rather than simple homogeneous catalyst.

The combined method can minimize soap formation by using heterogeneous catalyst and trace level of $CH_3ONa$ and can overcome the limitations of the heterogeneous catalysts. After about 8 hours the yields were slightly decreased because of side reactions. Two possible side reactions are free fatty acid neutralization and saponification. The free fatty acid neutralization was minimal since the acid number of the oil was about 0.046 mg KOH/g. Consequently, saponification is the main possible side reaction. It was observed that the saponification reaction was increased after most of the glycerides were consumed. Thus, there is an optimum reaction time attaining the maximum biodiesel production.

Referring to FIG. 2 again, the conversion versus time curves of Marathon MSA and Marathon A were illustrated. Marathon MSA (macroporous resin) showed a high catalytic activity without adding $CH_3ONa$ and then levels off. On the other hand, Marathon A (gel type resin) showed a low activity at the entire reaction period, although its basic site density was high at about 1.70 mmol/g compared to Marathon MSA (about 0.50 mol/g). The high catalytic activity of the Marathon MSA can be attributed to the macroporous nature where large molecules can access. Although the initial activities of macroporous resins (Marathon MSA) were higher than those of gel phase resins (Marathon A), the final activities, however, were similar. It is attributed to the higher basic site densities of the gel type resins. This means that the gel type resin could afford larger number of hydroxide ions to the reaction medium in a basic environment than the macroporous type resin.

The Influence of Internal Structure of Resin on Catalytic Activity

Figure 3:
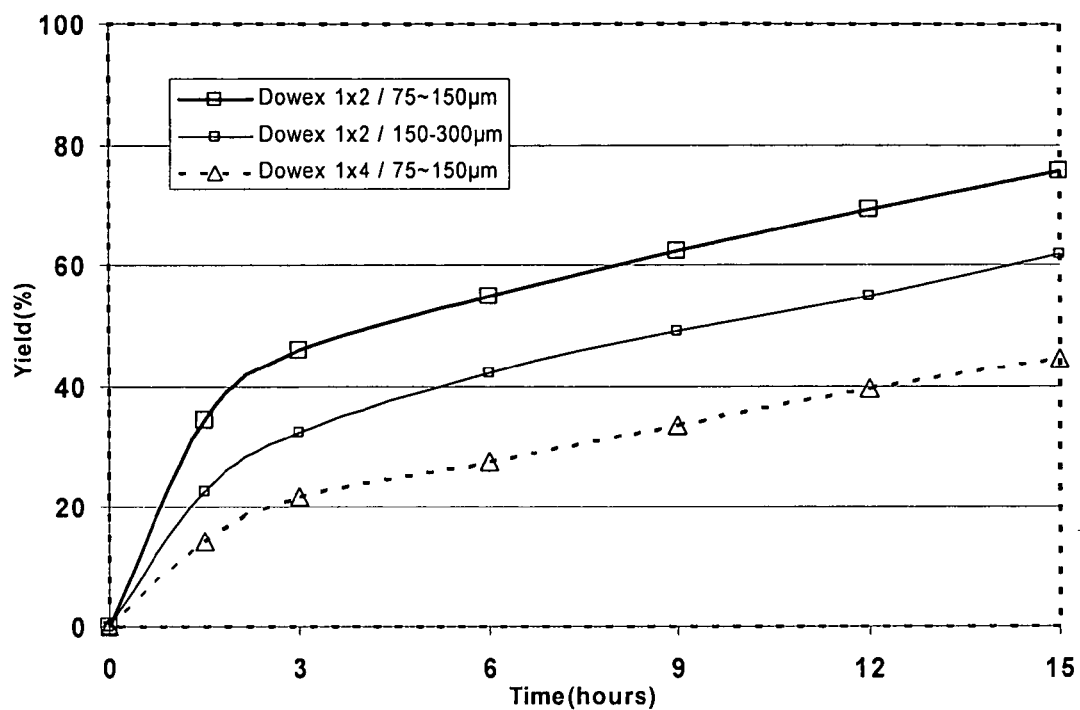
FIG. 3 is a diagram illustrating the influence of internal structure of resin on catalytic activity.

Referring to FIG. 3, high initial catalytic activities were observed from the macroporous resins such as Amberite 900 and Marathon MSA due to the large surface areas (about 500 $m^2/g$) of the macroporous structure. However, the gel type of resins (Marathon A, Monosphere 550A) showed linear and low reaction rates with reaction time. Although the gel type resins have three times higher basic site density than the macroporous structure resins, the catalytic activities of the gel type resins were low without the aid of $CH_3ONa$. This means the gel type resin which has low amounts of macropores where triglyceride can access. The reaction was carried out with acidic soybean oil (about 30 g), a methanol/oil molar ratio of about 10:1, at a reaction temperature of about 326 K, and a shaking speed of about 350 rpm.

The Effects of Catalyst Concentration on Reaction Yield

Figure 4:
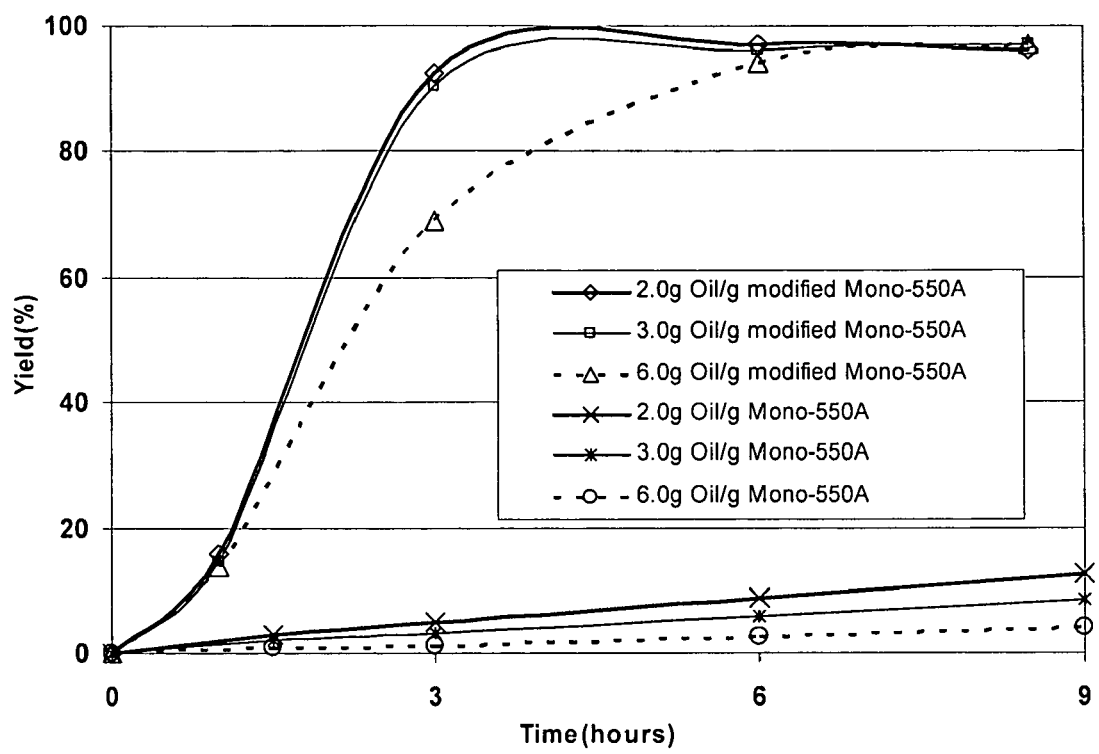
FIG. 4 is a diagram illustrating the influence of catalyst amounts on the catalytic activity.

Referring to FIG. 4, if all of the basic sites of about 10.0 g of the resin catalyst (Monosphere 550A) were available for about 30.0 g of soybean oil, the equivalent NaOH wt % to soybean oil was about 1.95%. However, increasing concentrations of homogeneous catalyst to more than about 1% NaOH is not effective and lead to decrease yields, presumably because of side reactions (soap formation). Only limited portion of basic sites of the gel type resin (Monosphere 550A) could contribute to catalyze the transesterification reaction in neutral or acidic environment. This result means that only limited basic sites located on outer surface of the resins can catalyze transesterification. Furthermore, some of the basic sites can be ion exchanged with organic anions such as oleates and linoleates generated during reaction. These large organic anions may block the micropore opening of the resins. Thus, the activity of resins was low. The reaction was carried out with a Monosphere 550A catalyst, about 30.0 g soybean oil, about 5.1 mL of about 0.02 M $CH_3ONa$ in methanol, a methanol/oil molar ratio of about 10:1, at a reaction temperature of about 328 K, a shaking speed of about 350 rpm.

However, organic anions can be converted to biodiesel through further reaction with methanol in a basic medium. Thus, catalytic activity of the surface can be sustained. Moreover, strong basic sites located in micropores can afford active hydroxide ions continuously. Thus, the reaction rate was proportionally increased with increasing catalyst weight because the activity of the basic sites of the resin was restricted in acidic or neutral environment. However, in a basic environment the reaction rate increased with increasing the amount of catalyst till about 3.0 g oil/g catalyst. However, further increase in the amount of catalyst did not bring proportional difference in conversion.

Figure 5:
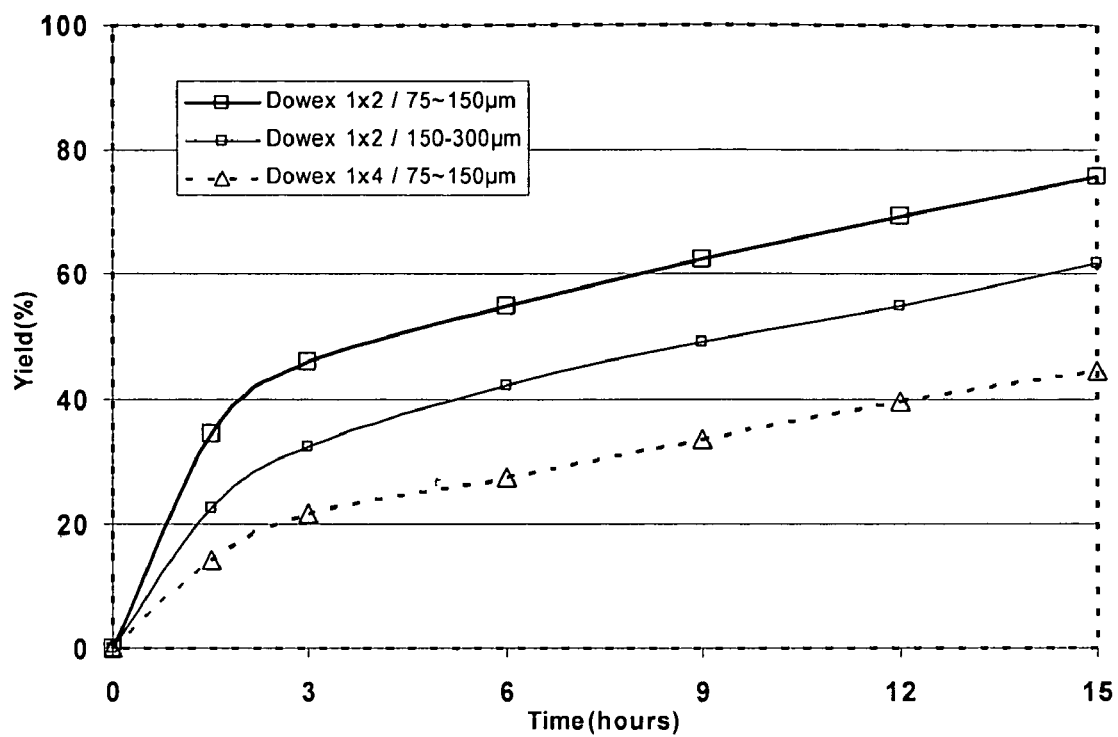
FIG. 5 is a diagram illustrating the influences of degree of cross-linking and particle size on the catalytic activity.

The Influence of Cross-Linking and Particle Size of the Resins on the Catalytic Activity Referring to FIG. 5, Dowex 1×2 and 1×4 resins have about 2% and about 4% cross-linked structures, respectively. The degree of cross-linking in the resin determines pore size and basic site density of the resin beads. The porosity of gel type resins is inversely related to the degree of cross-linking of divinylbenzene. Macroporous resins are generally highly cross-linked. With the same range of particle sizes (about 75~150 μm), Dowex 1×2 had a higher catalytic activity than Dowex 1×4 resin. This suggests that the resin which has a lower cross-linking has larger pores and a higher basic site density. The lowest cross-linking density and the smallest particle size gave the highest reaction rate. The reaction was carried out with about 30 g of acidic soybean oil, about 10.0 g of resin catalyst, a methanol/oil molar ratio of about 10:1, at a reaction temperature of about 326 K, and a shaking speed of about 350 rpm.

The Effect of Methanol to Oil Ratio on the Yield

Figure 6A:
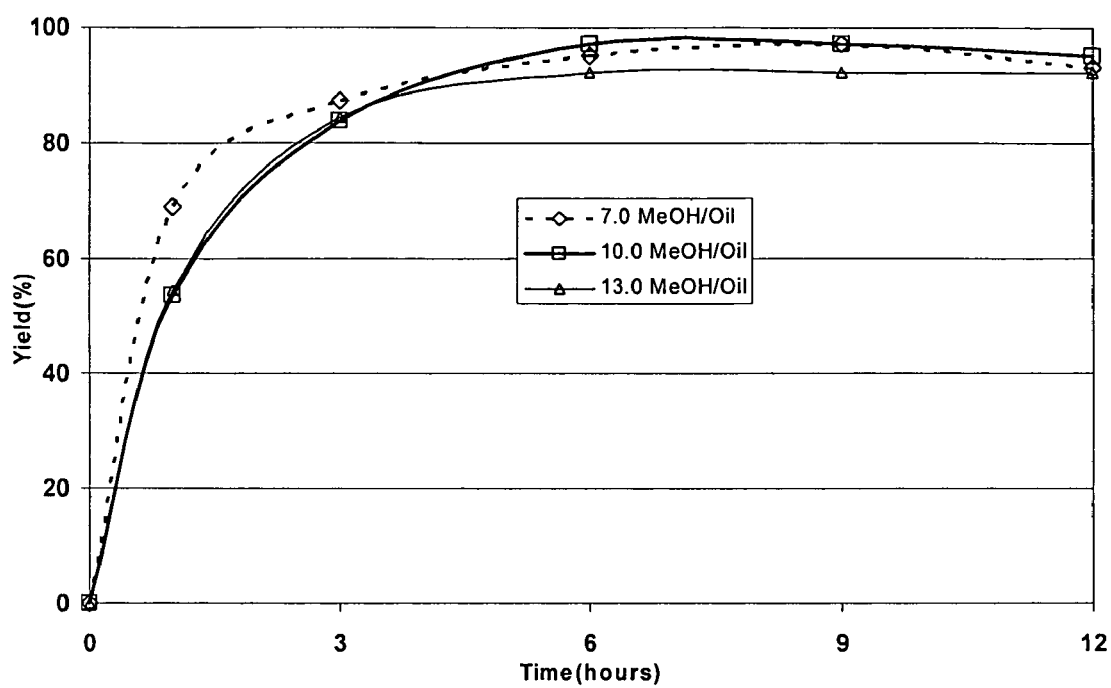
FIG. 6A is a diagram illustrating the effect of methanol/oil molar ratio on the conversion of soybean oil with methanol to biodiesel using Marathon MSA.
Figure 6B:
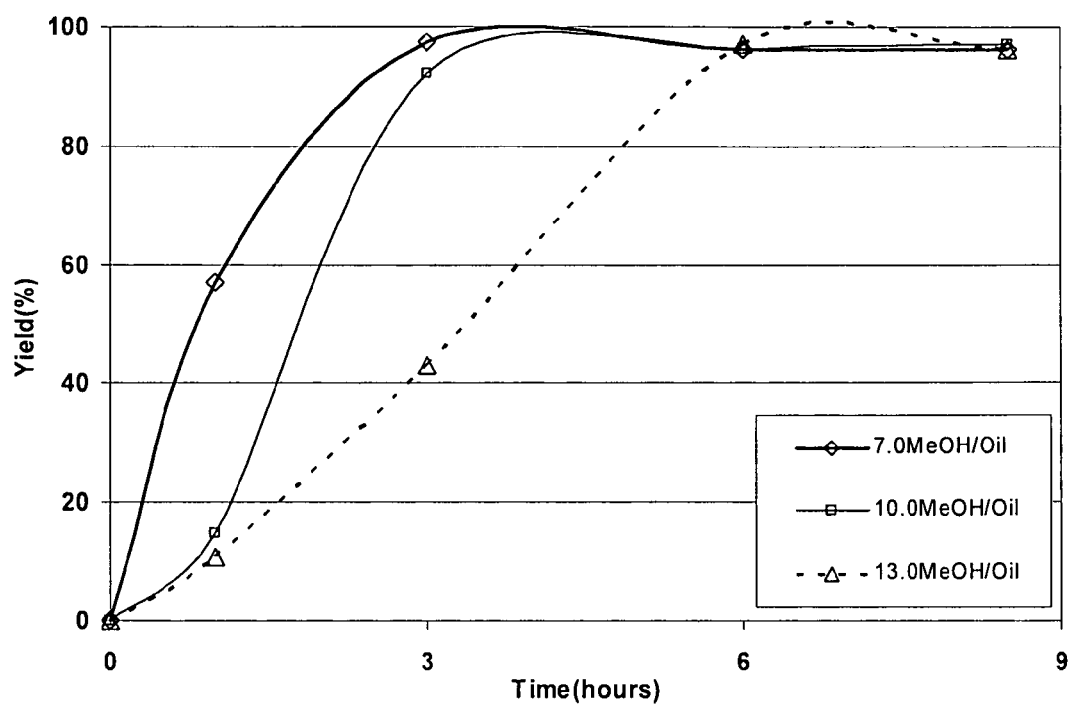
FIG. 6B is a diagram illustrating the effect of methanol/oil molar ratio on the conversion of soybean oil with methanol to biodiesel using Monosphere 550A.

Referring to FIG. 6, stoichiometric molar ratio of methanol to soybean oil in the transesterification of soybean oil with methanol is about 3:1. However, in practice a higher molar ratio is employed in order to shift the reaction equilibrium towards the product side and produce more methyl esters. For example, a maximum conversion about 67% was obtained when the molar ratio was close to about 15:1 with a reaction time of about 9 hours, the potassium loaded alumina catalyst amount of about 7.5%, and at about 65° C. Alternatively, the conversion reached the maximum value of about 87% on a solid base catalyst ZnO loaded with KF when the methanol/oil ratio was close to about 10:1. Alternatively, a maximum conversion was obtained at the molar ratio (methanol/oil) of about 20:1 and almost the same conversion was attained at the molar ratio of about 10:1, and reaction time of about 9 hours at about 65° C.

Referring to FIG. 6 again, the initial reaction rate was highest at the molar ratio about 7:1. At the final stage when the reaction went toward completion, the mixture with the molar ratio of about 10:1 had higher reaction rate than the mixture with the molar ratio of about 7:1. The mixture with the molar ratio of about 13:1 showed the lowest reaction rate for the entire reaction period. At the initial reaction excess methanol cause to decrease chances of collision between reactants and catalyst, so the lower reaction rate was observed at higher methanol to oil ratio. Similar final conversions were resulted from the methanol to oil ratios of both about 10:1 and about 7:1. This combined method need a lower methanol to oil ratio compared to other heterogeneous catalysts because some portion of the conversion was resulted from the homogeneous mechanism. The reaction was carried out with about 30 g of soybean oil, about 5.1 mL of about 0.02 M $CH_3ONa$ solution in methanol, about 10.0 g of resin catalyst (Marathon MSA in FIG. 6A and Monosphere 550A in FIG. 6B), at a reaction temperature of about 326 K, a shaking speed of about 350 rpm.

The Deactivation and Regeneration of Resin Catalysts

Figure 7A:
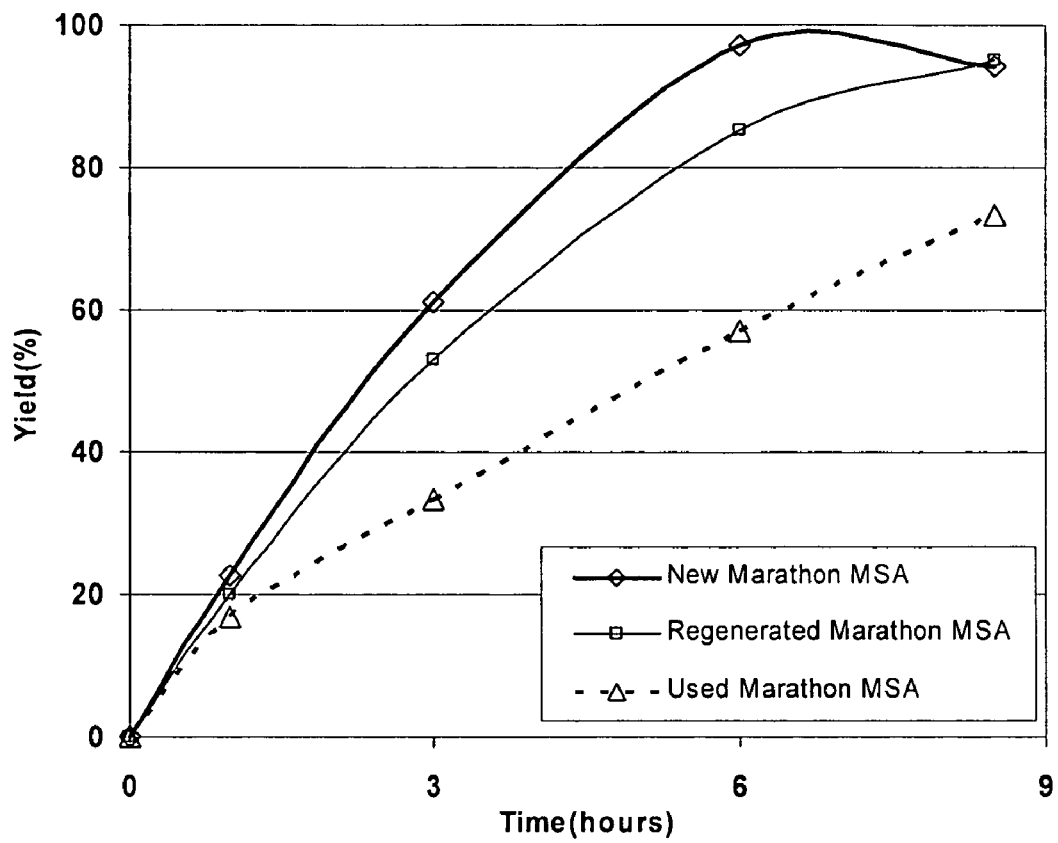
FIG. 7A is a diagram illustrating the catalytic activities of the new (ion-exchanged), used, and regenerated Marathon MSA resin catalyst (ion exchanged after used).
Figure 7B:
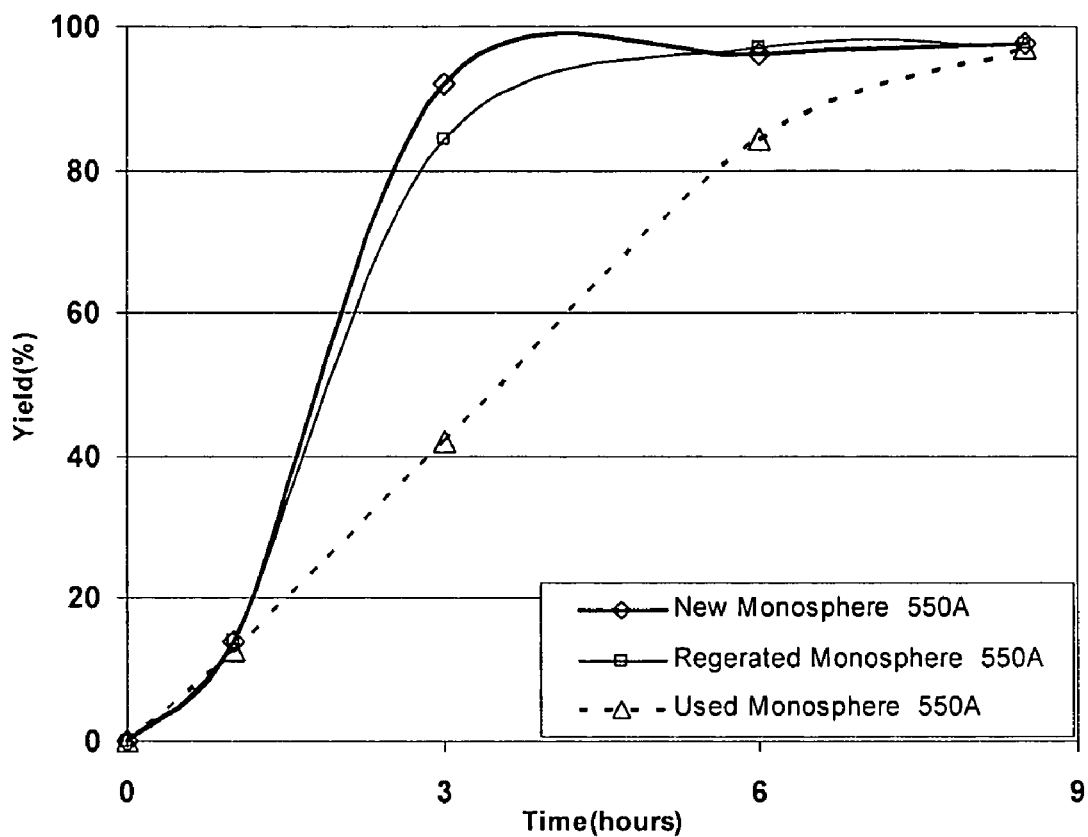
FIG. 7B is a diagram illustrating the catalytic activities of the new (ion-exchanged), used, and regenerated Monosphere 550A resin catalyst (ion exchanged after used).

Referring to FIG. 7, the catalytic activity of the used Marathon MSA was about half of the fresh catalyst. The regenerated Marathon MSA and Monosphere 550A showed lower catalytic activities than the fresh ones. Macroporous resin (Marathon MSA) showed poorer regeneration efficiency and higher regeneration cost than the gel type resin (Monosphere 550A). This difference may be attributed to both thermal decomposition of ammonium sites of the resin and the resin ion-exchanged with organic anion. The regenerated Marathon A showed the nearly same activity with the fresh one. The gel type resins have a merit in the regeneration of the used catalyst. The reaction was carried out with about 30 g of soybean oil, about 5.1 mL of about 0.020 M $CH_3ONa$ solution in methanol, about 10 g of resin catalyst (Marathon MSA in FIG. 7A and Monosphere 550A in FIG. 7B), a methanol/oil molar ratio of about 10:1, at a reaction temperature of about 328 K, a shaking speed of about 350 rpm.

A viable heterogeneous catalytic process for transesterification of biodiesel is disclosed. In this novel method, only trace level of homogeneous catalyst, such as NaOH or $CH_3ONa$ (for example about 0.02%), is used. The novel method decreased the side reactions caused by homogeneous base catalysts. Thus, the method minimizes separation, corrosion and environmental problems, and maximizes yields through using a trace level of homogeneous catalyst. The amount of water needed for the washing process is minimized as well. The combining method using both homogeneous and heterogeneous catalysts in the transesterification process is compatible with realizing heterogeneous catalyst in industrial biodiesel production.

While the invention has been described with reference to certain embodiments, other features may be included without departing from the spirit and scope of the invention. It is therefore intended that the foregoing detailed description be regarded as illustrative rather than limiting, and that it be understood that it is the following claims, including all equivalents, that are intended to define the spirit and scope of this invention.

The invention claimed is:

1. A process for producing a biofuel, the process comprising:
   reacting a feed material that comprises a glyceride with an alcohol in the presence of a catalytic composition such that at least some of the glyceride in the feed material is converted into a biofuel mixture that comprises glycerol and the corresponding alcoholic ester of the glyceride,
   wherein the catalytic composition comprises a heterogeneous catalyst and a homogeneous catalyst, and
   wherein the heterogeneous catalyst and the homogeneous catalyst have a synergistic effect in catalyzing the reaction of the glyceride in the feed material with the alcohol.

2. The process for producing a biofuel of claim 1, wherein the homogeneous catalyst is a co-catalyst that maintains a local basic environment in which the heterogeneous catalyst is activated.

3. The process for producing a biofuel of claim 1, wherein the feed material comprises a fatty acid triglyceride.

4. The process for producing a biofuel of claim 1, wherein the feed material comprises a material selected from the group consisting of a vegetable oil, an animal fat, and combinations thereof.

5. The process for producing a biofuel of claim 1, wherein the heterogeneous catalyst is selected from the group consisting of an anion exchange resin, a cation exchange resin, a metal oxide, and combinations thereof.

6. The process for producing a biofuel of claim 5, wherein the anion exchange resin is selected from the group consisting of a gel type anion exchange resin, a macroporous type anion exchange resin, and combinations thereof.

7. The process for producing a biofuel of claim 5, wherein the heterogeneous catalyst is selected from the group consisting of tin oxide, magnesium oxide, zinc oxide, hydrotalcite, zeolite loaded with sodium oxide, Li/CaO, KF/ZnO, $Zn/I_2$, potassium loaded alumina, mixed metal oxides, and combinations thereof.

8. The process for producing a biofuel of claim 1, wherein the homogeneous catalyst is selected from the group consisting of an alkali compound, an alkali earth compound, and combinations thereof.

9. The process for producing a biofuel of claim 8, wherein the alkali compound is selected from the group consisting of NaOH, KOH, $Ca(OH)_2$, and combinations thereof.

10. The process for producing a biofuel of claim 8, wherein the alkali compound is $CH_3ONa$.

11. The process for producing a biofuel of claim 1, wherein the homogeneous catalyst is no more than about 1% of the feed material weight.

12. The process for producing a biofuel of claim 11, wherein the homogeneous catalyst is no more than about 0.02% of the feed material weight.

13. The process for producing a biofuel of claim 1, wherein the mass ratio of the catalyst composition to the feed material is about 1:3.

14. The process for producing a biofuel of claim 1, wherein the molar ratio of the alcohol to the feed material is from about 1:1 to about 20:1.

15. The process for producing a biofuel of claim 14, wherein the molar ratio of the alcohol to the feed material is about 7:1.

16. The process for producing a biofuel of claim 1, wherein the reacting step comprises:
    contacting the feed material with the heterogeneous catalyst;
    heating the feed material and the heterogeneous catalyst;
    adding the alcohol and the homogeneous catalyst to the feed material and the heterogeneous catalyst to obtain a reaction mixture; and
    allowing the reaction mixture to react.

17. The process for producing a biofuel of claim 16, wherein the allowing step comprises incubating the reaction mixture for a period of time such that a substantial portion of the glyceride in the feed material is converted into the corresponding alcoholic ester of the glyceride before a saponification side reaction is substantially started.

18. The process for producing a biofuel of claim 1, further comprising:
    removing some or substantially all of the glycerol from the biofuel mixture to produce the biofuel.

19. A process for producing a biofuel, the process comprising:
    contacting a feed material that comprises a glyceride with a heterogeneous catalyst;
    heating the feed material and the heterogeneous catalyst;
    adding an alcohol and a homogeneous catalyst to the feed material and the heterogeneous catalyst; and
    allowing the glyceride in the feed material and the alcohol to react to produce the corresponding alcoholic ester of the glyceride.

20. A process for producing a biofuel, the process comprising:
    converting a feed material that comprises a glyceride, in the presence of an alcohol, into glycerol and the corresponding ester of the glyceride using a heterogeneous resin catalyst combined with a homogeneous catalyst.

* * * * *